United States Patent
Moriyama

(10) Patent No.: US 11,931,098 B2
(45) Date of Patent: Mar. 19, 2024

(54) SYSTEM AND METHOD FOR CARRYING OUT A MEDICAL PROCEDURE

(71) Applicant: Boston Scientific Medical Device Limited, Ballybrit (IE)

(72) Inventor: Eduardo Moriyama, Richmond (CA)

(73) Assignee: Boston Scientific Medical Device Limited, Ballybrit (IE)

( * ) Notice: Subject to any disclaimer, the term of this patent is extended or adjusted under 35 U.S.C. 154(b) by 1042 days.

(21) Appl. No.: 16/794,799

(22) Filed: Feb. 19, 2020

(65) Prior Publication Data
US 2021/0251686 A1    Aug. 19, 2021

(51) Int. Cl.

| | |
|---|---|
| A61B 18/14 | (2006.01) |
| A61B 5/1455 | (2006.01) |
| A61B 5/1459 | (2006.01) |
| A61B 17/00 | (2006.01) |
| A61B 18/00 | (2006.01) |
| A61B 90/30 | (2016.01) |
| A61M 25/09 | (2006.01) |

(52) U.S. Cl.
CPC ...... *A61B 18/1477* (2013.01); *A61B 5/14552* (2013.01); *A61B 5/1459* (2013.01); *A61B 2017/00057* (2013.01); *A61B 2017/00119* (2013.01); *A61B 2017/00247* (2013.01); *A61B 2018/0038* (2013.01); *A61B 2018/00601* (2013.01); *A61B 2090/306* (2016.02); *A61M 25/09* (2013.01)

(58) Field of Classification Search
CPC ............ A61B 18/1477; A61B 18/1492; A61B 2017/00057; A61B 2017/00061; A61B 2017/00119; A61B 2017/00247; A61B 2018/00351; A61B 2018/0038; A61B 2018/00601; A61B 2018/00613; A61B 2018/00642; A61B 2018/00708; A61B 2090/306; A61B 2505/05; A61B 5/14552; A61B 5/1459; A61B 5/6848; A61B 5/6852; A61B 5/6869; A61B 90/30; A61M 25/09

See application file for complete search history.

(56) References Cited

U.S. PATENT DOCUMENTS

| | | |
|---|---|---|
| 175,254 A | 3/1876 | Oberly |
| 827,626 A | 7/1906 | Gillet |
| 848,711 A | 4/1907 | Weaver |
| 1,072,954 A | 9/1913 | Junn |

(Continued)

*Primary Examiner* — Michael F Peffley
(74) *Attorney, Agent, or Firm* — Nelson Mullins Riley & Scarborough LLP

(57) ABSTRACT

A medical system includes a medical device and an analysis system. The medical device includes a perforation device having a shaft. The shaft has a proximal portion, and an opposed distal portion. A perforating tip is associated with the distal portion. At least a first light emitter is associated with the distal portion and is positioned proximate the perforating tip for illuminating a region surrounding the perforating tip. The analysis system is for analyzing returned light that is returned towards the shaft from the region surrounding the perforating tip. The analysis system includes a light sensor configured to detect one or more parameters of the returned light, a processor configured to perform an analysis of the one or more parameters, and an alert system connected to the processor for alerting a user to a result of the analysis.

21 Claims, 7 Drawing Sheets

(56) References Cited

U.S. PATENT DOCUMENTS

| | | |
|---|---|---|
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |

(56) References Cited

U.S. PATENT DOCUMENTS

| | | |
|---|---|---|
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,270,662 B2 * | 9/2007 | Visram ............... A61B 18/1492 606/41 |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,749,217 B2 * | 7/2010 | Podhajsky ......... A61B 18/1402 606/41 |
| 7,828,796 B2 | 11/2010 | Wong et al. |
| 7,900,928 B2 | 3/2011 | Held et al. |
| 8,123,745 B2 * | 2/2012 | Beeckler ............... A61B 5/1459 606/41 |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 8,577,447 B2 * | 11/2013 | Tegg .................... A61B 5/6886 606/41 |
| 8,986,292 B2 * | 3/2015 | Sliwa .................... A61B 5/0075 606/15 |
| 8,986,298 B2 * | 3/2015 | Lee .................... A61B 18/1492 606/41 |
| 10,194,981 B2 * | 2/2019 | Margallo Balbás . A61B 5/0059 |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McIntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Violante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0275439 A1 | 11/2008 | Francischelli et al. |
| 2009/0105742 A1 | 4/2009 | Kurth et al. |
| 2009/0138009 A1 | 5/2009 | Viswanathan et al. |
| 2009/0156921 A1 * | 6/2009 | Wang ................. A61B 5/14542 606/41 |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |

(56) References Cited

U.S. PATENT DOCUMENTS

| | | |
|---|---|---|
| 2010/0194047 A1 | 8/2010 | Sauerwine |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0206987 A1 | 7/2014 | Urbanski et al. |
| 2014/0296769 A1 | 10/2014 | Hyde et al. |
| 2016/0220741 A1 | 8/2016 | Garrison et al. |
| 2019/0021763 A1 | 1/2019 | Zhou et al. |
| 2019/0110838 A1* | 4/2019 | Martinez ............... A61B 90/30 |
| 2019/0216503 A1* | 7/2019 | Otsubo ............. A61B 17/3421 |
| 2019/0247035 A1 | 8/2019 | Gittard et al. |

* cited by examiner

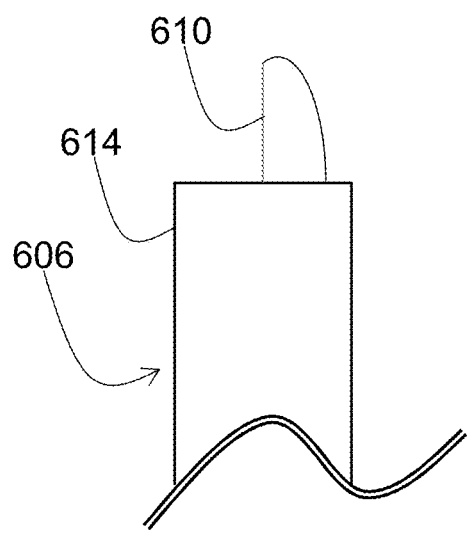
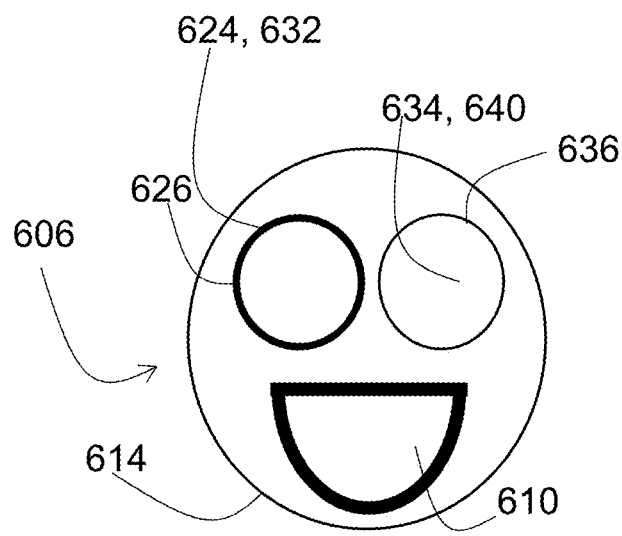
FIGURE 6
FIGURE 7
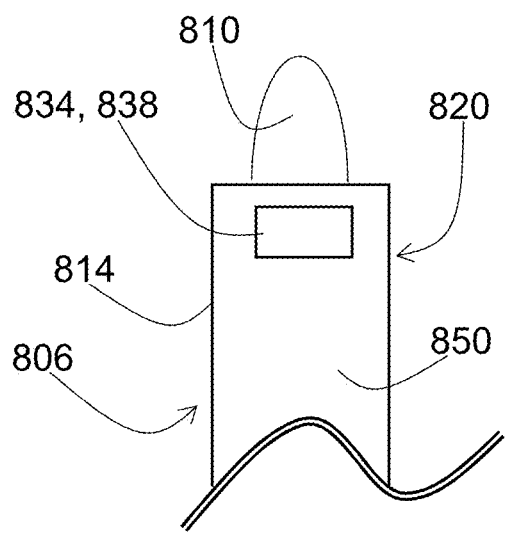
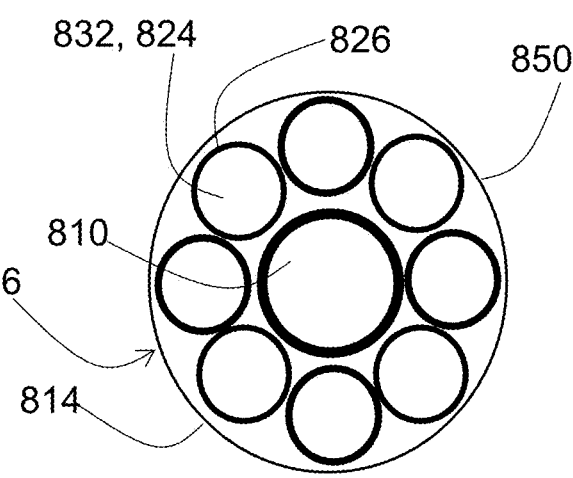
FIGURE 8
FIGURE 9

SYSTEM AND METHOD FOR CARRYING OUT A MEDICAL PROCEDURE

FIELD

This document relates to medical procedures such as transseptal perforation. More specifically, this document relates to devices for use in such medical procedures, and related systems and methods.

SUMMARY

The following summary is intended to introduce the reader to various aspects of the detailed description, but not to define or delimit any invention.

Perforation devices for use in medical procedures are disclosed. According to some aspects, a perforation device includes a shaft. The shaft has a proximal portion, and an opposed distal portion. A perforating tip is associated with the distal portion. At least a first light emitter is associated with the distal portion and is positioned proximate the perforating tip, for illuminating a region surrounding the perforating tip. At least a first light collector is associated with the distal portion and is positioned proximate the perforating tip, for collecting light from the region surrounding the perforating tip.

In some examples, the perforation device further includes at least a first illumination optical fiber extending through the shaft from the proximal portion to the distal portion. The illumination optical fiber has a source end for receiving light from a light source and an illumination end proximate the perforating tip. The illumination end forms the light emitter.

In some examples the perforation device further includes at least a first collection optical fiber extending through the shaft from the proximal portion to the distal portion. The collection optical fiber has a light collection end that forms the light collector, and a sensor end for delivering light to a light sensor.

In some examples, the light collector is in the form of a light sensor associated with the distal portion of the shaft.

In some examples, the perforating tip includes a radiofrequency perforation electrode.

In some examples, the illumination end is shrouded within the shaft, and the perforation device further includes a light scattering material between the illumination end and an opening in the shaft for directing light from the illumination end to an exterior of the shaft.

In some examples, the illumination end is distally facing. In some examples, the illumination end is recessed proximally from a distal end face of the shaft. In some examples, the illumination end is flush with a distal end face of the shaft.

Medical systems are also disclosed. According to some aspects, a medical system includes a perforation device. The perforation device includes a perforation device having a shaft. The shaft has a proximal portion, and an opposed distal portion. A perforating tip is associated with the distal portion. At least a first light emitter is associated with the distal portion and is positioned proximate the perforating tip for illuminating a region surrounding the perforating tip. The medical system further includes an analysis system for analyzing returned light that is returned back towards the shaft from the region surrounding the perforating tip. The analysis system includes a light sensor configured to detect one or more parameters of the returned light, a processor configured to perform an analysis of the one or more parameters, and an alert system connected to the processor for alerting a user to a result of the analysis.

In some examples, the medical system includes a light source, and at least a first illumination optical fiber extending through the shaft from the proximal portion to the distal portion. The illumination optical fiber has a source end connected to the light source for receiving light from the light source, and an illumination end positioned proximate the perforating tip and forming the light emitter.

In some examples, the medical system further includes a first collection optical fiber extending through the shaft from the proximal portion to the distal portion. The collection optical fiber has a light collection end for collecting the returned light, and a sensor end for delivering light to the sensor.

In some examples, the sensor is mounted to the distal portion of the shaft.

In some examples, the result is an indication of whether blood in the region surrounding the perforating tip is oxygenated blood or deoxygenated blood.

In some examples, the perforating tip includes a radiofrequency perforation electrode. The medical system can further include a radio frequency generator connected to the radiofrequency perforation electrode for powering the radiofrequency perforation electrode. The generator can be in communication with the analysis system and can be configured to provide power to the radiofrequency perforation electrode based on the analysis. The generator can be configured to cease providing power to the radiofrequency perforation electrode if the analysis indicates that the region surrounding the perforating tip contains oxygenated blood.

Methods for carrying out medical procedures are also disclosed. According to some aspects, a method for carrying out a medical procedure includes a. positioning a perforating tip of a puncture device adjacent a target region within a patient's body; b. advancing the perforating tip through the target region; c. before, during and/or after step b., illuminating a region surrounding the perforating tip with light, collecting light returned back from the region surrounding the perforating tip, and analyzing the returned light.

In some examples, the method further includes ceasing advancement of the perforating tip if the analysis of the returned light indicates that the region surrounding the perforating tip contains oxygenated blood.

In some examples, the method further includes continuing or repeating advancement of the perforating tip if the analysis of the returned light indicates that the region surrounding the perforating tip contains deoxygenated blood.

In some examples, step b. includes delivering radiofrequency energy to the perforating tip to puncture the fossa ovalis. In some examples, the method further includes ceasing the delivery of radiofrequency energy if the analysis of the returned light indicates that the region surrounding the perforating tip contains oxygenated blood.

In some examples, the target region is a fossa ovalis.

BRIEF DESCRIPTION OF THE DRAWINGS

The accompanying drawings are for illustrating examples of articles, methods, and apparatuses of the present disclosure and are not intended to be limiting. In the drawings:

FIG. 6 is a partial side view of another example perforation device;

FIG. 7 is an end view of the perforation device of FIG. 6;

FIG. 8 is a is a partial side view of another example perforation device;

FIG. 9 is an end view of the perforation device of FIG. 8;

DETAILED DESCRIPTION

Various apparatuses or processes or compositions will be described below to provide an example of an embodiment of the claimed subject matter. No example described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Generally disclosed herein are devices and systems that can be used in medical procedures, such as cardiac procedures. For example, the devices systems can be used in transseptal perforation procedures, in which a sheath is advanced to the right atrium of a patient's heart via the femoral vein, and a perforation device (e.g. a radiofrequency (RF) perforation device or a mechanical perforation device) and dilator are guided through the sheath, to the right atrium. When the sheath is adjacent a target region in the right atrium, for example the fossa ovalis of the atrial septum, the perforation device can be advanced out of the sheath and used to create a perforation in the target region, and the dilator can be advanced out of the sheath to dilate the perforation. Such procedures can be carried out, for example, as a medical treatment, or to gain access to the left atrium for a subsequent medical treatment.

Figure 1:
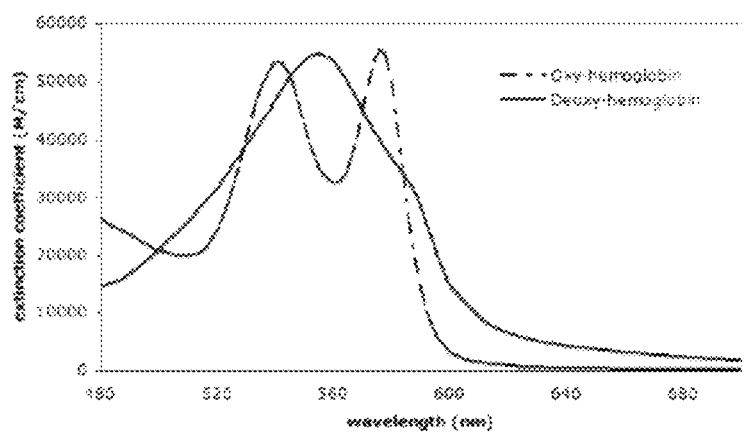
FIG. 1 shows an example absorption spectrum for oxyhemoglobin and hemoglobin.

The systems, devices, and methods disclosed herein can be used to determine whether perforation is complete—i.e. whether the perforation device has indeed perforated the atrial septum and the perforating tip is in the left atrium, or whether perforation is not yet complete and the perforating tip is within the atrial septum, still within the right atrium, or elsewhere. This can in turn reduce the use of fluoroscopy, decrease the complication rate in such procedures, and enhance patient safety. Particularly, the systems and devices disclosed herein are configured to emit light to (i.e. illuminate) the region surrounding the perforating tip of the perforation device, and to collect light that is returned from the region surrounding the perforating tip (referred to herein as "returned light", which can be, for example, reflected light or emitted fluorescence). This returned light is then analyzed, for example using absorption or fluorescence spectroscopy. Particularly, blood that is within the right atrium is venous blood, which is not oxygenated and largely contains deoxyhemoglobin. In contrast, blood that is within the left atrium is arterial blood, which is oxygenated and largely contains oxyhemoglobin. Deoxyhemoglobin and oxyhemoglobin have distinct absorption spectra in the range of 520 nm and 600 nm, as shown in FIG. 1. By analyzing the absorption spectrum of the light returned from the region surrounding the perforating tip, it can be determined whether this region largely contains deoxyhemoglobin or oxyhemoglobin, and in turn it can be determined whether the perforating tip is in the right atrium (which contains largely deoxyhemoglobin) or the left atrium (which contains largely oxyhemoglobin).

Figure 2:
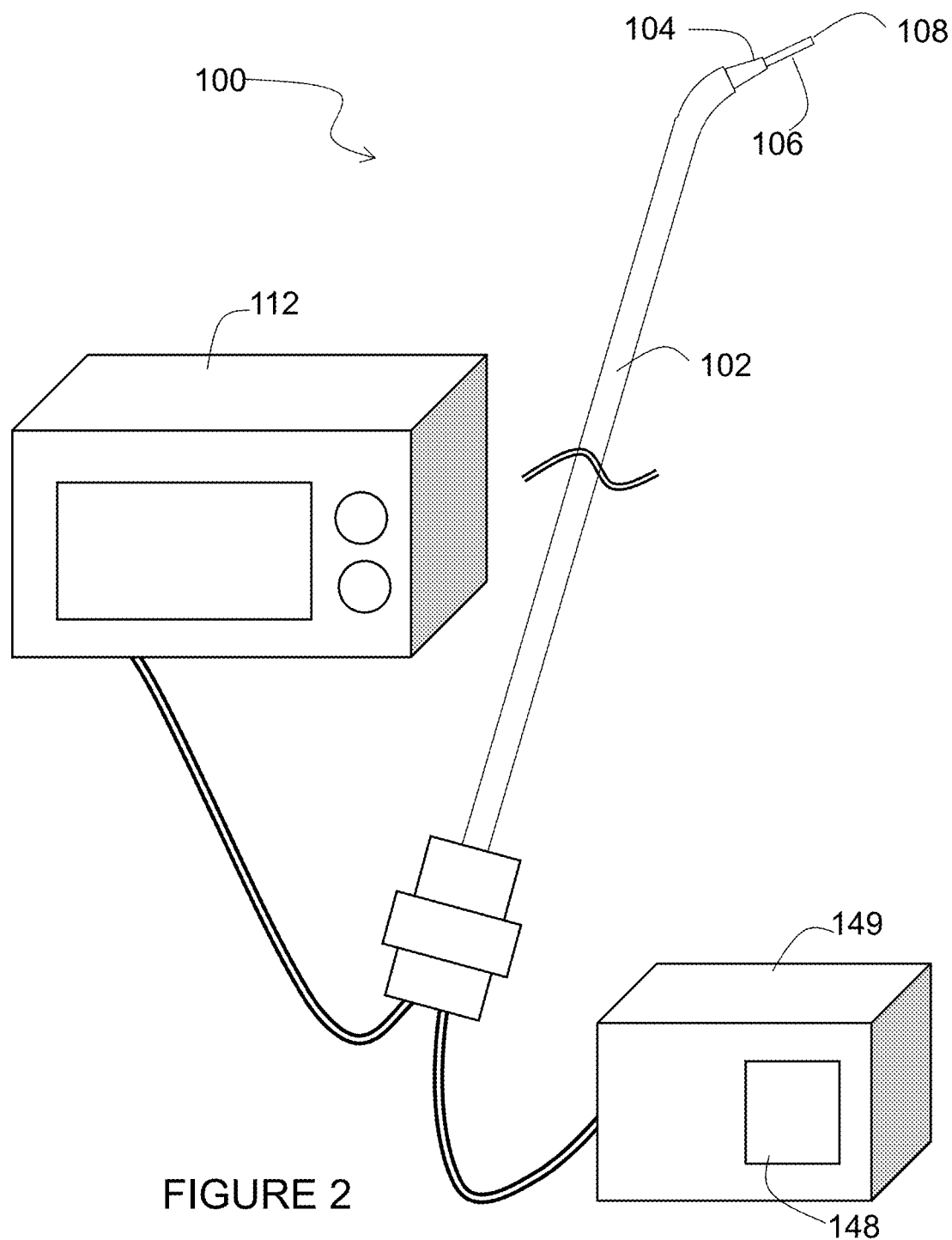
FIG. 2 is a perspective view of an example medical system.

Referring now to FIG. 2, an example medical system 100 is shown. In the example shown, the system 100 is a transseptal perforation system, for advancing towards a patient's heart and perforating a fossa ovalis of the patient's heart. The system includes a set of medical devices, including a sheath 102, a dilator 104, and a perforation device 106 having a perforating tip 108. In the examples shown, the perforation device 106 is a radiofrequency (RF) perforation device, and the perforating tip 108 includes a radiofrequency electrode 110 (shown in FIG. 3).

In use, the sheath 102 can be advanced intravenously via the femoral vein towards the right atrium of the patient's heart. The dilator 104 and perforation device 106 can both be advanced towards the patient's heart via the sheath 102. The RF perforation device 106 can be connected to a radiofrequency generator 112, which can in turn be connected to one or more grounding pads (not shown). When in the desired position in the patient's heart, for example adjacent the fossa ovalis, the RF perforation device 106 can be activated to perforate the fossa ovalis.

Figure 3:
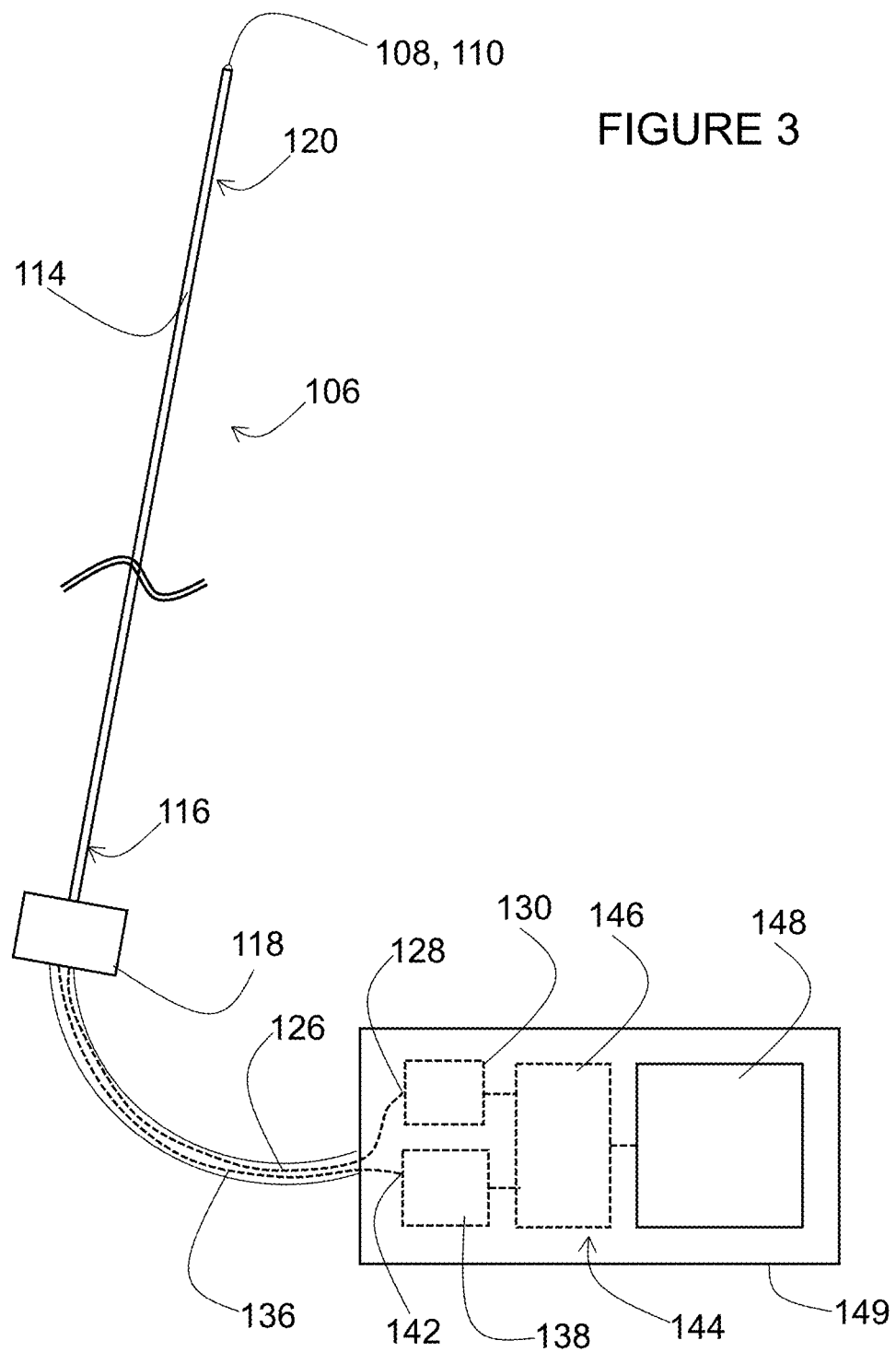
FIG. 3 is a perspective view of the perforation device of the medical system of FIG. 2.
Figure 4:
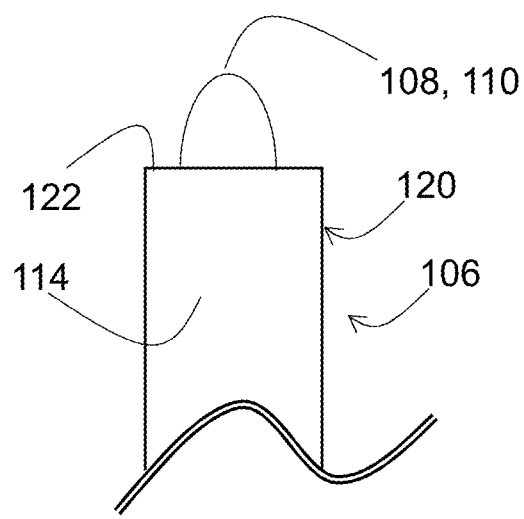
FIG. 4 is a partial side view of the perforation device of FIG. 3.
Figure 5:
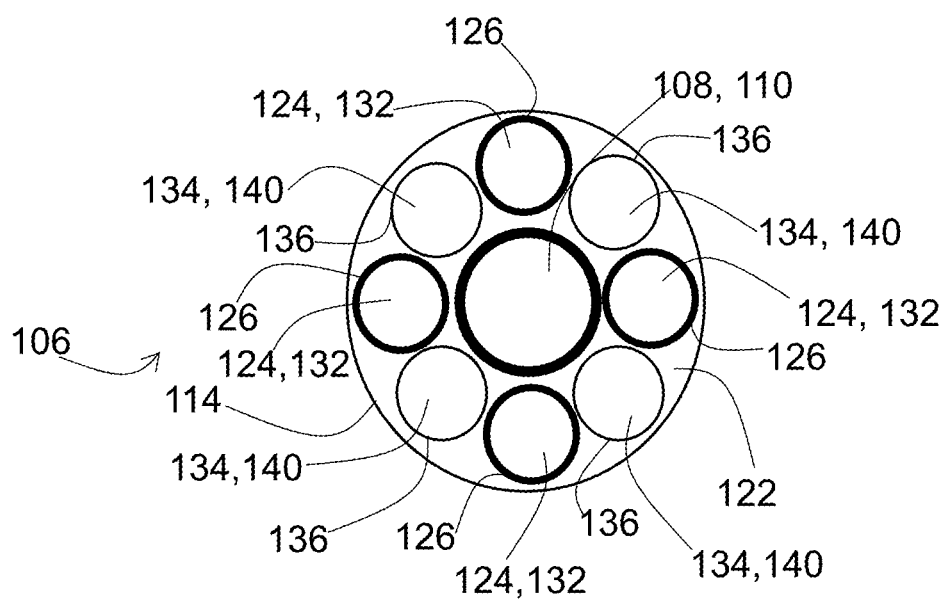
FIG. 5 is an end view of the perforation device of FIG. 3.

Referring to FIGS. 3 to 5, the perforation device 106 is shown in greater detail. In the example shown, the perforation device 106 includes a shaft 114, which can be, for example, fabricated from a plastic. The shaft 114 has a proximal portion 116 that is connected to a hub 118, and an opposed distal portion 120. The perforating tip 108 is associated with the distal portion 120 of the shaft 114. As used herein, the term "associated with" means that the first referenced part (i.e. in this case the perforating tip 108) and second referenced part (i.e. in this case the shaft 114) are configured so that the first referenced part moves with the second referenced part. For example, the first referenced part can be mounted to, extend from, adhered to, embedded in, part of, formed by, and/or integral with second referenced part. In the example shown, the perforating tip 108 includes the radiofrequency perforation electrode 110, which is secured to and extends distally from a distal face 122 of the shaft 114. An electrical connector (not shown) is connected to and extends proximally from the radiofrequency perforation electrode 110 through the shaft 114, for connection to the radiofrequency generator 112 (not shown in FIGS. 3 to 5)

The perforation device 106 further includes a set of light emitters 124 associated with the distal portion 120 of the shaft 114 and positioned proximate the perforating tip 108 for illuminating the region surrounding the perforating tip 108 (i.e. for delivering light to blood or tissue that is in contact with or near to the perforating tip 108). The light emitters 124 can be of various configurations. Referring to FIG. 5, in the example shown, the perforation device 106 includes a first set of optical fibers, referred to herein to as "illumination optical fibers 126". The illumination optical fibers 126 are embedded in the shaft 114 and extend through the shaft 114 from the proximal portion 116 to the distal portion 120. For example, the illumination optical fibers 126 can be embedded in dedicated channels within the shaft 114. In alternative examples, the shaft 114 can have a lumen, and the illumination optical fibers 126 can extend through the lumen, and be sealed within the lumen by an epoxy or glue.

Referring to FIG. 3 (in which only one of the illumination optical fibers 126 is shown, and is shown only partially), the illumination optical fibers 126 each have a first end 128 (referred to herein as a "source end") that is connected or connectable to a light source 130 (described below), for receiving light from the light source 130. Referring back to FIG. 5, the illumination optical fibers 126 further have a second end 132 (referred to herein as an "illumination end") proximate the perforating tip 108. The illumination end 132 of each illumination optical fiber 126 forms a light emitter 124, and illuminates the region surrounding the perforating tip 108. In the example shown, the illumination end 132 of each illumination optical fiber 126 is flush with the distal end face 122 of the shaft 114, and is distally facing. In alternative examples, the illumination end 132 of the illumination optical fibers 126 can be recessed proximally from the distal end face 122 of the shaft 114, or can extend proud of the distal end face 122 of the shaft 114.

Referring still to FIG. 5, the perforation device 106 further includes a set of light collectors 134 associated with the distal portion 120 of the shaft 114 and positioned proximate the perforating tip 108, for collecting light returned from the region surrounding the perforating tip 108 (also referred to herein as "returned light"). For example, the returned light can be reflected light or emitted fluorescence. The light collectors 134 can be of various configurations. In the example shown, the perforation device 106 includes a second set of optical fibers, referred to herein as "collection optical fibers 136", for collecting light returned from the region surrounding the perforating tip 108 and delivering the returned light to a light sensor 138 (described below). The collection optical fibers 136 are embedded in the shaft 114 and extend through the shaft 114 from the distal portion 120 to the proximal portion 116. For example, the collection optical fibers 136 can be embedded in dedicated channels within the shaft 114. In alternative examples, the shaft 114 can have a lumen, and the collection optical fibers 136 can extend through the lumen, and be sealed within the lumen by an epoxy or glue.

Referring still to FIG. 5, the collection optical fibers 136 each have a first end 140 (referred to herein as a "light collection end") that forms the light collector 134. In the example shown, the collection end 140 of the collection optical fibers 136 is flush with the distal end face 122 of the shaft 114, and is distally facing. In alternative examples, the collection end 140 of the collection optical fibers 136 can be recessed proximally from the distal end face 122 of the shaft 114, or can extend proud of the distal end face 122 of the shaft 114. Referring to FIG. 3 (in which only one of the collection optical fibers 136 is shown, and is shown only partially), the collection optical fibers 136 further have a second end 142 (referred to herein as an "sensor end") for delivering light to the light sensor 138.

Referring still to FIGS. 3 to 5, in the example shown, the illumination optical fibers 126 and collection optical fibers 136 are arranged concentrically around the RF electrode 110 in an alternating pattern. In other examples, as will be described below, the illumination optical fibers 126 and collection optical fibers 136 can be of another arrangement.

Referring still to FIG. 3, the light source 130 can be, for example, a laser, a lamp (e.g. an Xe or Arc lamp), or an LED. The light source 130 can be monochromatic or broad band. The light delivered by the light source 130 can be continuous or pulsed (e.g. pulsed by a pulse generator or light chopper).

Referring still to FIG. 3, the system 100 includes an analysis system 144 for analyzing the returned light. The analysis system 144 includes the light sensor 138, which can be any suitable sensor that can detect one or more parameters (e.g. the absorption or fluorescence spectrum) of the returned light. For example, the light sensor 138 can be or can include a photodiode, a power meter, a spectrometer, a phototransistor, and/or a photomultiplier. The light sensor 138 can be a single chip or multi-chip detector. The light sensor 138 can include a CCD or CMOS camera.

The analysis system 144 further includes a processor 146 connected to the light sensor. The processor 146 can include various hardware and software, and is configured to perform an analysis of the parameters detected by the light sensor 138. For example, the processor 146 can compare the absorption spectrum of the returned light to a stored reference absorption spectrum for oxyhemoglobin and deoxyhemoglobin. Based on this comparison, the processor 146 can then determine whether the absorption spectrum of the returned light corresponds to the reference spectrum for oxyhemoglobin (which indicates that the region surrounding the perforating tip 108 contains oxygenated blood) or deoxyhemoglobin (which indicates that the region surrounding the perforating tip 108 contains deoxygenated blood).

The analysis system 144 further includes an alerting system connected to the processor 146, for alerting a user to a result of the analysis. In the example shown, the alerting system includes a screen 148 that displays an indicium of the position of the perforating tip 108. Alternatively, the alerting system can be, for example, in the form of a light that changes color when the analysis indicates that the region surrounding the perforating tip 108 contains oxygenated blood. The change in color of the light can indicate to a user that the perforating tip 108 is in the left atrium. Alternatively, the alerting system can provide an auditory alert that indicates to a user that the perforating tip 108 is in the left atrium.

In the example shown, the light source 130, light sensor 138, processor 146, and screen 148 are provided in a single unit 149. In alternative examples, the light source 130, light sensor 138, processor 146, and screen 148 may be provided in separate units or at separate locations. For example, the light sensor 138 may be mounted to the perforation device 106 (as described below), and the processor 146 and screen 148 may be provided in a separate unit. Alternatively, one or more of the light source 130, light sensor 138, processor 146, and screen 148 may be provided in a unit with the RF generator 112.

Optionally, the RF generator 112 (shown in FIG. 2) can be in communication with the analysis system 144, and can be configured to provide power to the RF electrode 110 based on the analysis. For example, the RF generator 112 can be configured to provide power to the RF electrode 110 only while the analysis indicates that the region surrounding the perforating tip 108 contains deoxygenated blood. Alternatively, the RF generator 112 can be configured to cease providing power to the RF electrode 110 if the analysis indicates that the region surrounding the perforating tip 108 contains oxygenated blood. This may further enhance safety, as once perforation of the fossa ovalis is complete, perforation of additional structures will be prevented (or the risk thereof will be reduced).

Referring now to FIGS. 6 and 7, another example of a perforation device is shown. In FIGS. 6 and 7, features that are similar to those of FIGS. 1 to 5 are referred to with like reference numerals, incremented by 500. The perforation device 606 of FIGS. 6 and 7 includes only one light emitter 624, in the form of an illumination end 632 of an illumination optical fiber 626, and only one light collector 634, in the form of a collection end 640 of a collection optical fiber 636. The light emitter 624 and light collector 634 are positioned side-by-side and adjacent the RF electrode 610, and are and off-centre within the shaft 614. The illumination optical fiber 626 and collection optical fiber 636 have a larger diameter than the corresponding parts of FIGS. 1 to 5.

Referring now to FIGS. 8 and 9, another example of a perforation device is shown. In FIGS. 8 and 9, features that are similar to those of FIGS. 1 to 5 are referred to with like reference numerals, incremented by 700. In the example of FIGS. 8 and 9, similarly to the example of FIGS. 1 to 5, the perforation device 806 includes a set of illumination optical fibers 826, the illumination ends 832 of which form light emitters 824 (only one of the illumination optical fibers 826 is labelled in FIG. 9). The illumination optical fibers 826 are arranged concentrically around the RF electrode 810.

In the example of FIGS. 8 and 9, collection optical fibers are omitted, and the light collector 834 is in the form of a light sensor 838 associated with the distal portion 820 of the shaft 814. In the example shown, the light sensor 838 is mounted to a side surface 850 of the shaft 814. An electrical connector (not shown) extends through the shaft 814 to connect the light sensor 838 to the processor (not shown) of the analysis system (not shown). The light sensor 838 can be any suitable sensor that can detect one or more parameters (e.g. the absorption or fluorescence spectrum) of the returned light. For example, the light sensor 838 can be or can include a photodiode, a power meter, a spectrometer, a phototransistor, and/or a photomultiplier. The light sensor 838 can be a single chip or multi-chip detector. The light sensor 838 can include a CCD or CMOS camera.

Figure 10:
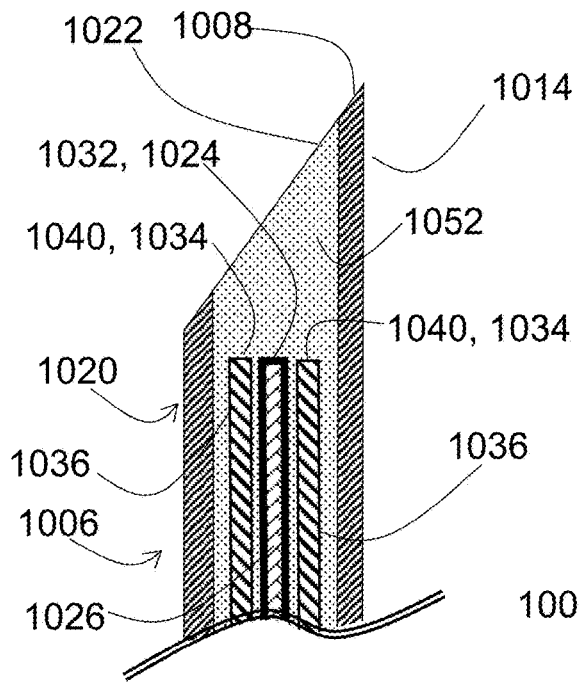
FIG. 10 is a longitudinal cross-section taken through another example perforation device.
Figure 11:
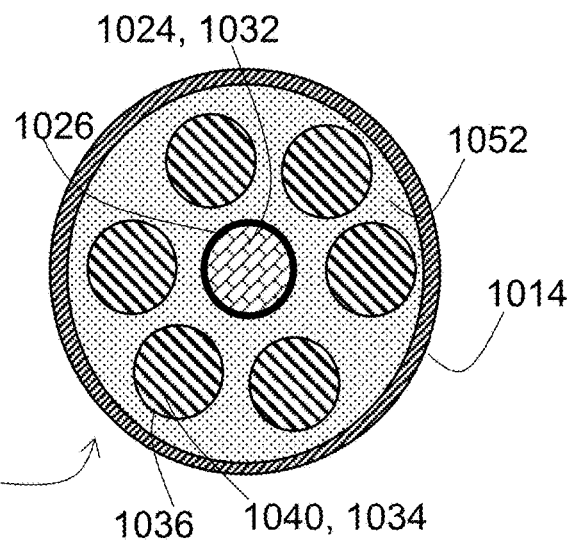
FIG. 11 is transverse cross-section taken through the perforation device of FIG. 10.

Referring now to FIGS. 10 and 11, another example of a perforation device is shown. In FIGS. 10 and 11, features that are similar to those of FIGS. 1 to 5 are referred to with like reference numerals, incremented by 900. In the example of FIGS. 10 and 11, the perforation device 1006 is a mechanical perforation device, in which the distal portion 1020 of the shaft 1014 is beveled to provide a sharp perforating tip 1008. The perforation device 1006 includes an illumination optical fiber 1026, the illumination end 1032 of which forms a light emitter 1024, and a set of collection optical fibers 1036 (only one of which is labelled in FIG. 11), the collection ends 1040 of which form light collectors 1034. The illumination optical fiber 1026 and the collection optical fibers 1036 are positioned within a lumen of the shaft 1014, and the illumination end 1032 and collection ends 1040 are recessed proximally from the distal end face 1022 of the shaft 1014. A light transmitting material 1052 such as an epoxy or glue seals the lumen.

In the example of FIGS. 10 and 11, the perforating device 1006 includes a single illumination optical fiber 1026 and six collection optical fibers 1036. In other examples, another number of illumination optical fibers and collection fibers can be used.

Figure 12:
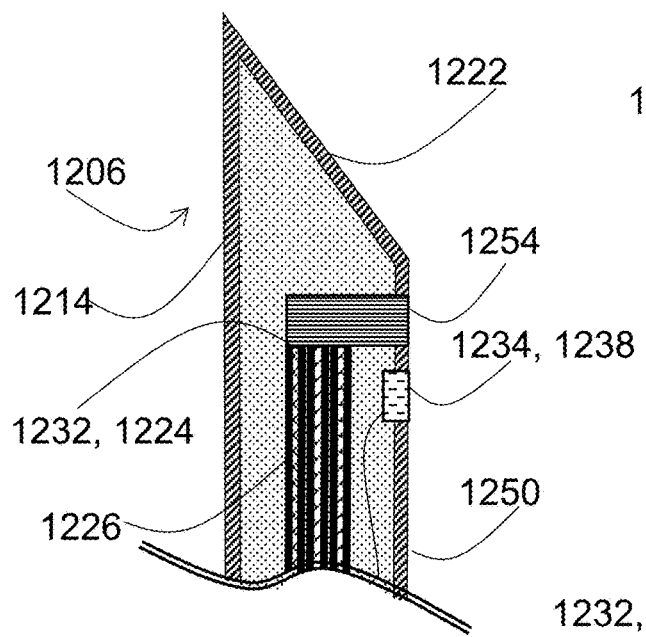
FIG. 12 is a longitudinal cross-section taken through another example perforation device.
Figure 13:
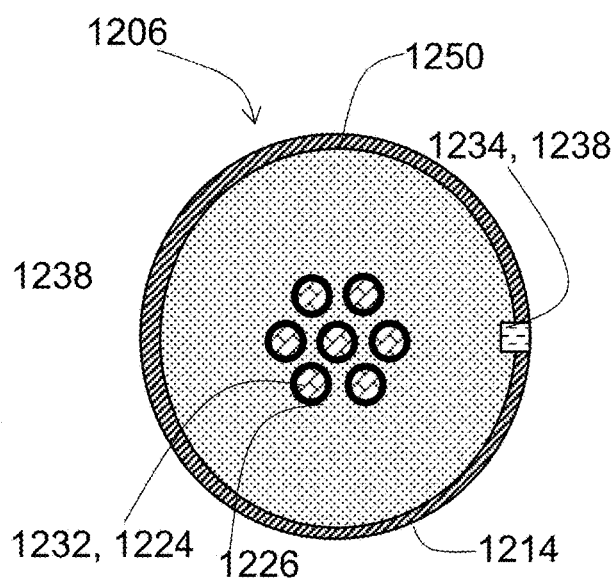
FIG. 13 is transverse cross-section taken through the perforation device of FIG. 12.

Referring now to FIGS. 12 and 13, another example of a perforation device is shown. In FIGS. 12 and 13, features that are similar to those of FIGS. 1 to 5 are referred to with like reference numerals, incremented by 1100. In the example of FIGS. 12 and 13, the perforation device 1206 includes a set of illumination optical fiber 1226 (only one of which is labelled), the illumination ends 1232 of which form light emitter 1224. The illumination ends 1232 are shrouded within the shaft 1214, the distal end face 1222 of which is closed. A light scattering material 1254 is positioned within the shaft 1214, between the illumination ends 1232 and an opening on the side surface 1250 of the shaft 1214. The light scattering material 1254 directs light radially from the illumination ends 1232 to the exterior of the shaft 1214.

In the example of FIGS. 12 and 13, the light collector 1234 is in the form of a light sensor 1238 that is mounted to the side surface 1250 of the shaft 1214, proximate to the light scattering material 1254.

A method for transseptal perforation will now be described with reference to FIGS. 14 to 16. The method will be described with reference to the system of FIGS. 1 to 5; however, the system of FIGS. 1 to 5 can be used according to different methods, and the method can employ different systems.

As a first step (not shown), a guidewire can be advanced via the femoral vein towards the heart, and "parked" in the superior vena cava (SVC). The dilator 104 can then be inserted into the sheath 102, with the tip of the dilator 104 shrouded within the sheath 102. The sheath 102 and dilator 104 can then be advanced over the guidewire, towards the SVC. The guidewire can then be removed.

As a second step (not shown), the perforation device 106 can be advanced through the dilator 104, until the perforating tip 108 is just shy of the distal end of the dilator 104.

Figure 14:
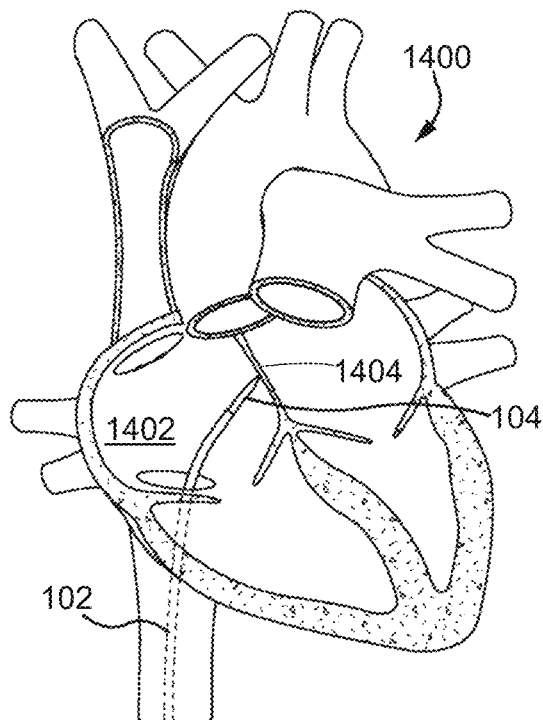
FIG. 14 shows a step of a method using the system of FIG. 2.
Figure 15:
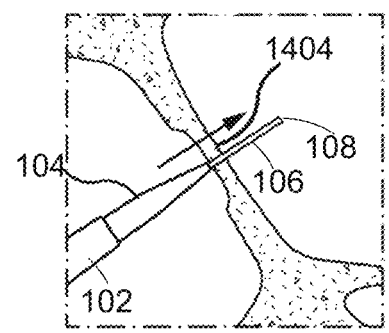
FIG. 15 shows another step of a method using the system of FIG. 2.

Referring to FIG. 14, as a third step, the distal end of the sheath 102 can then be advanced towards a target location in the patient's heart 1400, e.g. to the right atrium 1402 of the patient's heart 1400, to position the distal end of the sheath 102 adjacent the target location. In the example shown, the target location is the fossa ovalis 1404 of the atrial septum. The dilator 104 can then be advanced so that the dilating end thereof is proud of the sheath 102, and the perforation device 106 (not visible in FIG. 14) can be advanced so that the perforating tip 108 is proud of or flush with the dilator 104 and is adjacent the fossa ovalis 1404. This positioning is shown in FIG. 14

With the perforation device 106 in the ready position, as shown in FIG. 14, The light source 130 (not shown in FIGS. 14 to 16) and analysis system 144 (not shown in FIGS. 14 to 16) can then be engaged, to confirm the positioning of the perforating tip 108. Particularly, the light source 130 can be engaged to illuminate the region surrounding the perforating tip 108, and the returned light can be collected and analyzed to determine whether the region surrounding the perforating tip 108 contains oxygenated blood or deoxygenated blood. If the analysis indicates that the region surrounding the perforating tip 108 contains oxygenated blood, this indicates that the perforating tip 108 is not properly positioned, and the procedure can be stopped or the position of the perforation device 106 can be adjusted or checked using imaging.

If the analysis indicates that the region surrounding the perforating tip 108 contains deoxygenated blood, this indicates that the perforating tip 108 is properly positioned, and the procedure can continue.

To continue the procedure, the RF generator 112 (not shown in FIGS. 14 to 16) can be engaged, to supply power to the RF electrode 110. The perforating tip 108 can then be advanced through the fossa ovalis 1404, as shown in FIG. 15. During and/or after advancement of the perforating tip 108, the position of the perforating tip 108 can be monitored and/or confirmed. That is, the light source 130 can be engaged to illuminate the region surrounding the perforating tip 108, and the returned light can be collected and analyzed to determine whether the region surrounding the perforating tip 108 contains oxygenated blood or deoxygenated blood. If the analysis indicates that the region surrounding the perforating tip 108 contains oxygenated blood, this indicates that the perforating tip 108 has perforated the fossa ovalis 1404 and is in the left atrium, and the advancement of the perforating tip 108 and the delivery of RF energy can be ceased. If the analysis indicates that the region surrounding the perforating tip 108 contains deoxygenated blood, this indicates that the perforating tip 108 has not perforated the fossa ovalis 1404, and advancement of the perforating tip 108 and delivery of RF energy should continue or be repeated.

Optionally, before or during advancement of the perforating tip 108 through the fossa ovalis, the fluorescence spectra of the tissue of the fossa ovalis 1404 can be obtained using an excitation wavelength of about 365 nm. Due to the presence of collagen and other fluorophores within the fossa ovalis 1404, a distinct fluorescence spectrum may be obtained at this wavelength. This can be used to confirm that the perforating tip is within or in contact with the fossa ovalis 1404.

Figure 16:
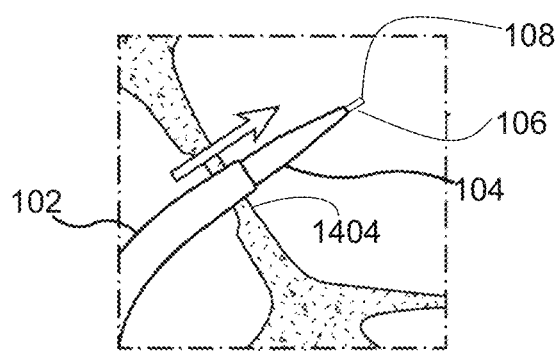
FIG. 16 shows another step of a method using the system of FIG. 2.

Referring to FIG. 16, once the fossa ovalis 1404 has been perforated, the dilator 104 can be advanced from the sheath 102 to dilate the perforation, and the sheath 102 can then be advanced through the perforation, to the left atrium. Once access to the left atrium has been gained, a subsequent medical treatment (not shown) can be carried out.

In alternative examples, other anatomical regions can be perforated using the devices, systems, and methods disclosed herein. For example, the devices, systems, and methods disclosed herein can be used to create channels between vessels (i.e. artery to vein or vice versa) and/or in ventricular puncture.

While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

I claim:

1. A perforation device for use in transseptal perforation procedures, comprising:
    a shaft, the shaft having a proximal portion and an opposed distal portion, the distal portion including a distal face;
    a dilator associated with the distal portion, positioned within the shaft;
    a perforating tip, comprising a radio frequency perforation electrode, associated with the distal portion and protruding from the distal face;
    at least a first light emitter, defining an illumination end associated with the distal portion and positioned proximate the perforating tip for illuminating a region surrounding the perforating tip, wherein the illumination end is disposed on the distal face surrounding the perforating tip; and
    at least a first light collector associated with the distal portion and positioned proximate the perforating tip for collecting light from the region surrounding the perforating tip.

2. The perforation device of claim 1, further comprising at least a first illumination optical fiber extending through the shaft from the proximal portion to the distal portion, the illumination optical fiber having a source end for receiving light from a light source and the illumination end proximate the perforating tip, wherein the illumination end forms the light emitter.

3. The perforation device of claim 1, further comprising at least a first collection optical fiber extending through the shaft from the proximal portion to the distal portion, the collection optical fiber having a light collection end that forms the light collector, and a sensor end for delivering light to a light sensor.

4. The perforation device of claim 1, wherein the light collector is in the form of a light sensor associated with the distal portion of the shaft.

5. The perforation device of claim 1, wherein the illumination end is shrouded within the shaft, and the perforation device further comprises a light scattering material between the illumination end and an opening in the shaft for directing light from the illumination end to an exterior of the shaft.

6. The perforation device of claim 1, wherein the illumination end is distally facing.

7. The perforation device of claim 1, wherein the illumination end is recessed proximally from a distal end face of the shaft.

8. The perforation device of claim 1, wherein the illumination end is flush with a distal end face of the shaft.

9. A medical system for providing transseptal punctures, the medical system comprising:
    a perforation device comprising i) a shaft, the shaft having a proximal portion and an opposed distal portion, the distal portion including a distal face that is perpendicular to the longitudinal axis, ii) a perforating tip comprising a radiofrequency perforation electrode, the perforating tip associated with the distal portion, and iii);
    at least a first light emitter associated with the distal face of the distal portion and positioned proximate the perforating tip for illuminating a region surrounding the perforating tip; and
    an analysis system for analyzing returned light that is returned back towards the shaft from the region surrounding the perforating tip, the analysis system comprising a light sensor configured to detect one or more parameters of the returned light, a processor configured to perform an analysis of the one or more parameters, and an alert system connected to the processor for alerting a user to a result of the analysis.

10. The medical system of claim 9, further comprising a light source, and at least a first illumination optical fiber extending through the shaft from the proximal portion to the distal portion, the illumination optical fiber having a source end connected to the light source for receiving light from the light source, and an illumination end positioned proximate the perforating tip and forming the light emitter.

11. The medical system of claim 9 wherein the perforation device further comprises a first collection optical fiber extending through the shaft from the proximal portion to the distal portion, the collection optical fiber having a light collection end for collecting the returned light, and a sensor end for delivering light to the sensor.

12. The medical system of claim 9, wherein the sensor is mounted to the distal portion of the shaft.

13. The medical system of claim 9, wherein one of the one or more parameters of analysis of the returned light is whether blood in the region surrounding the perforating tip is oxygenated blood or deoxygenated blood.

14. The medical system of claim 9, wherein
the medical system further comprises a radio frequency generator connected to the radiofrequency perforation electrode for powering the radiofrequency perforation electrode; and
the generator is in communication with the analysis system and is configured to provide power to the radiofrequency perforation electrode based on the analysis.

15. The medical system of claim 14, wherein the generator is configured to cease providing power to the radiofrequency perforation electrode if the analysis indicates that the region surrounding the perforating tip contains oxygenated blood.

16. A method for carrying out a transeptal puncture medical procedure, comprising:

a. positioning a perforating tip of a puncture device adjacent target region within a patient's body, wherein the perforating tip comprises a radiofrequency perforation electrode, wherein the distal portion including a distal face that is perpendicular to the longitudinal axis;
b. advancing the perforating tip through the target region;
c. advancing a dilator associated with the perforating tip through the target region;
d. before, during and/or after step b., illuminating a region surrounding the perforating tip with light from a light emitter associated with the distal face, collecting light returned from the region surrounding the perforating tip, and analyzing the returned light.

17. The method of claim 16, further comprising ceasing advancement of the perforating tip if the analysis of the returned light indicates that the region surrounding the perforating tip contains oxygenated blood.

18. The method of claim 16, further comprising continuing or repeating advancement of the perforating tip if the analysis of the returned light indicates that the region surrounding the perforating tip contains deoxygenated blood.

19. The method of claim 16, wherein step b. comprises delivering radiofrequency energy to the perforating tip to puncture the target region.

20. The method of claim 19, further comprising ceasing the delivery of radiofrequency energy if the analysis of the returned light indicates that the region surrounding the perforating tip contains oxygenated blood.

21. The method of claim 16, wherein the target region is a fossa ovalis.

* * * * *